(12) United States Patent
Jovanov et al.

(10) Patent No.: US 11,872,080 B1
(45) Date of Patent: Jan. 16, 2024

(54) MULTI-MODAL HEART DIAGNOSTIC SYSTEM AND METHOD

(71) Applicant: The Board of Trustees of the University of Alabama, for and on behalf of the University of Alabama in Huntsville, Huntsville, AL (US)

(72) Inventors: Emil Jovanov, Huntsville, AL (US); Nenad Filipovic, Kragujevac (YU)

(73) Assignee: Board of Trustees of the University of Alabama, for and on behalf of the University of Alabama in Huntsville, Huntsville, AL (US)

(*) Notice: Subject to any disclaimer, the term of this patent is extended or adjusted under 35 U.S.C. 154(b) by 393 days.

(21) Appl. No.: 17/187,172

(22) Filed: Feb. 26, 2021

Related U.S. Application Data (60) Provisional application No. 62/981,893, filed on Feb. 26, 2020.

(51) Int. Cl.
*A61B 8/00* (2006.01)
*A61B 8/08* (2006.01)
(Continued)

(52) U.S. Cl.
CPC .......... *A61B 8/4263* (2013.01); *A61B 5/0205* (2013.01); *A61B 5/7267* (2013.01); *A61B 8/0883* (2013.01); *A61B 8/4254* (2013.01); *A61B 8/461* (2013.01); *G05B 13/0265* (2013.01); *A61B 5/1102* (2013.01); *A61B 5/318* (2021.01); *A61B 7/04* (2013.01);
(Continued)

(58) Field of Classification Search
CPC .......... A61B 8/4263; A61B 2034/2051; A61B 2034/2048; A61B 6/0407; A61B 8/4245; A61B 8/4254; A61B 8/42; A61B 8/4227
See application file for complete search history.

(56) References Cited

U.S. PATENT DOCUMENTS

| 8,914,245 B2 | 12/2014 | Hopkins |
| 9,675,322 B2 | 6/2017 | Hoppmann et al. |

(Continued)

FOREIGN PATENT DOCUMENTS

EP  2818116 A1 * 12/2014 .......... A61B 8/4245

OTHER PUBLICATIONS

Ferng, "EchoNous KOSMOS 3-in-1 Ultrasound, Electronic Stethoscope, and ECG Helps with COVID-19," Medgadget, Sep. 2020, pp. 1-9.

(Continued)

*Primary Examiner* — Joel Lamprecht
*Assistant Examiner* — Ashish S Jasani
(74) *Attorney, Agent, or Firm* — Butler Snow LLP; Jon E. Holland (57) ABSTRACT

A multi-modal heart diagnostic system is provided. The diagnostic system can monitor heart activity and assists a user or operator in performing echocardiography. The system can include a positioning device that is placed on a patient's chest. The positioning device can incorporate several multi-modal sensors. The multi-modal sensors can measure different parameters associated with an assessment of heart activity. The multi-modal sensors can also be used to provide information that can assist an operator in positioning the probe within the positioning device to capture an echocardiogram.

16 Claims, 10 Drawing Sheets

(51) Int. Cl.
  *A61B 5/00*    (2006.01)
  *A61B 7/04*    (2006.01)
  *A61B 5/318*   (2021.01)
  *A61B 5/0205*  (2006.01)
  *G05B 13/02*   (2006.01)
  *A61B 5/11*    (2006.01)

(52) U.S. Cl.
  CPC .............. *A61B 2562/0219* (2013.01); *A61B 2562/0223* (2013.01)

(56) References Cited

U.S. PATENT DOCUMENTS

| | | | |
|---|---|---|---|
| 2008/0125646 A1* | 5/2008 | Govari | A61B 5/06 702/152 |
| 2012/0296216 A1* | 11/2012 | Sharf | A61B 8/4209 600/459 |
| 2018/0000405 A1* | 1/2018 | Penders | A61B 8/4416 |
| 2018/0153504 A1* | 6/2018 | Herickhoff | A61B 8/4472 |
| 2018/0263595 A1* | 9/2018 | Goksel | A61B 8/085 |
| 2019/0105019 A1* | 4/2019 | Pagoulatos | A61B 8/5284 |
| 2020/0113542 A1* | 4/2020 | Perrey | A61B 8/5207 |
| 2020/0178932 A1* | 6/2020 | Te Velde | A61F 13/024 |

OTHER PUBLICATIONS

Leng, et al., "The electronic stethoscope," BioMedical Engineering Online, 2015, pp. 1-37.

Savino, et al., "Handheld Ultrasound and Focused Cardiovascular Echography: Use and Information," Medicina, Jul. 2019, pp. 1-8, vol. 55,423.

\* cited by examiner

MULTI-MODAL HEART DIAGNOSTIC SYSTEM AND METHOD

CROSS-REFERENCE TO RELATED APPLICATION

This application claims the benefit of U.S. Provisional Patent Application No. 62/981,893, entitled "Multi Modal Heart Activity Sensor," filed on Feb. 26, 2020, which application is hereby expressly incorporated herein by reference in its entirety.

BACKGROUND

The present disclosure generally relates to a system and method that provides for monitoring of heart activity and assists a user in performing diagnostic procedures of the heart.

The heart function of a person can be assessed using multiple sensors (or modalities) and diagnostic procedures that are appropriate for evaluating different heart conditions. Some diagnostic procedures, which involve complex setups and are typically performed in medical facilities such as hospitals, can include magnetic resonance imaging (MRI) scans, positron emission tomography (PET) scans, computerized tomography (CT) or computerized axial tomography (CAT) scans, etc.

Other diagnostic procedures can include an electrocardiogram (ECG), auscultation and/or an echocardiogram (EC). ECGs can provide information about the heart's electrical activity. In addition to the monitoring of heart rhythms, ECGs can be used to diagnose myocardial ischemia and even localize part of the heart affected by the ischemic event. Auscultation, defined as listening to the heart sound, can be performed using acoustic sensors (e.g., a stethoscope) or electronically with a digital stethoscope (DS). Auscultation can be an important method for the early diagnosis of cardiac dysfunction. Traditional auscultation requires substantial clinical experience and good listening skills, while the DS has paved the way for a new field of computer-aided auscultation. An EC shows the shape and movement of heart valves, the size of heart chambers and their operation, and can be used to assess heart conditions, such as murmurs or damage to the heart due to prior heart attack or infection. During echocardiography, ultrasound (high-frequency sound waves) from a hand-held probe (also referred to as a wand or transducer) placed on a person's chest provides pictures of the hearts valves and chambers. While ECs can provide useful information for diagnosis, prognosis, and clinical and therapeutic management, the proper placement of the probe by the operator in order to obtain medically useful images can be time-consuming and uncomfortable to the person undergoing the procedure. In addition, traditional cardiac ultrasound (echocardiography) training requires a very long training period (e.g., 14 months of a full time training program) to develop the necessary skills and experience to obtain medically useful images. Due to the long training period, the training of less experienced staff (e.g., nurses) to record diagnostic images typically does not occur. Therefore, a system to assist an operator (including less experienced operators) in the placement of the probe during an EC to acquire high quality diagnostic images would be beneficial.

BRIEF DESCRIPTION OF THE DRAWINGS

The disclosure can be better understood with reference to the following drawings. The elements of the drawings are not necessarily to scale relative to each other, emphasis instead being placed upon clearly illustrating the principles of the disclosure. Furthermore, like reference numerals designate corresponding parts throughout the several views.

DETAILED DESCRIPTION

The present disclosure generally pertains to a system that provides for monitoring of heart activity and assists a user in performing diagnostic procedures of the heart. The system can include a positioning device that is placed on a person's (or patient's) chest. The positioning device can incorporate several multi-modal sensors and be used to assist an operator in positioning the probe for an echocardiogram (EC). The multi-modal sensors can measure different parameters associated with an assessment of heart activity. The multi-modal sensors can also be used to provide information that can assist an operator (including a non-expert operator) in positioning the probe for an EC. The use of the multi-modal sensors and the probe during a calibration procedure provides image information, position data, orientation data and other information that permits the system to determine an appropriate position for the probe for an EC and to provide subsequent guidance information to the operator of the system to enable the operator to position the probe in the appropriate position for the optimal EC diagnostic images. By having several multi-modal sensors and multiple sensing modalities, the system can provide improved signal quality and robustness of the monitoring of heart activity, as well as unique information obtained from the synergy of information from multiple sensing modalities. In addition, the system can implement real-time processing of information and artificial intelligence methods to provide further information and guidance to the operator to facilitate better diagnostic procedures and analysis.

In an embodiment, the system can include an integrated multi-node, multi-modal sensor setup that can be used to collect multiple sensory signals and the relative position of sensors in relation to organs and anatomical structures of the person. The system also has a method of presentation/ rendering of EC images from the probe that are placed on a physically accurate location on the body relative to the probe and the multi-modal sensor nodes. The system can represent an anatomically accurate physical location and view of underlying organs of the person in real time, as the position and orientation of the probe changes in time. The system also provides an integrated system that processes multi-modal signals and EC images to guide operators (or users) toward an optimal position and orientation of the probe that can produce quality diagnostic images and videos.

The system of the present disclosure can provide better and faster training of operators in obtaining diagnostic EC images and videos. The system also allows non-experts to take expert quality diagnostic images and videos. In addition, the system can provide automatic guidance to operators in order to optimize data collection using real-time processing of changes that may not be visible to the operator. A significant reduction of test duration can be provided by the system because of the faster sensor setup of already integrated multi-modal sensors and faster image/data acquisition using an automated expert system that provides guidance to the operator. The system can provide simultaneous acquisition and processing of multiple sensor modalities (e.g., electrical, sound, mechanical motion and ultrasound images) and can provide automatic calibration and adjustment according to the anatomy of individual patients.

Figure 1:
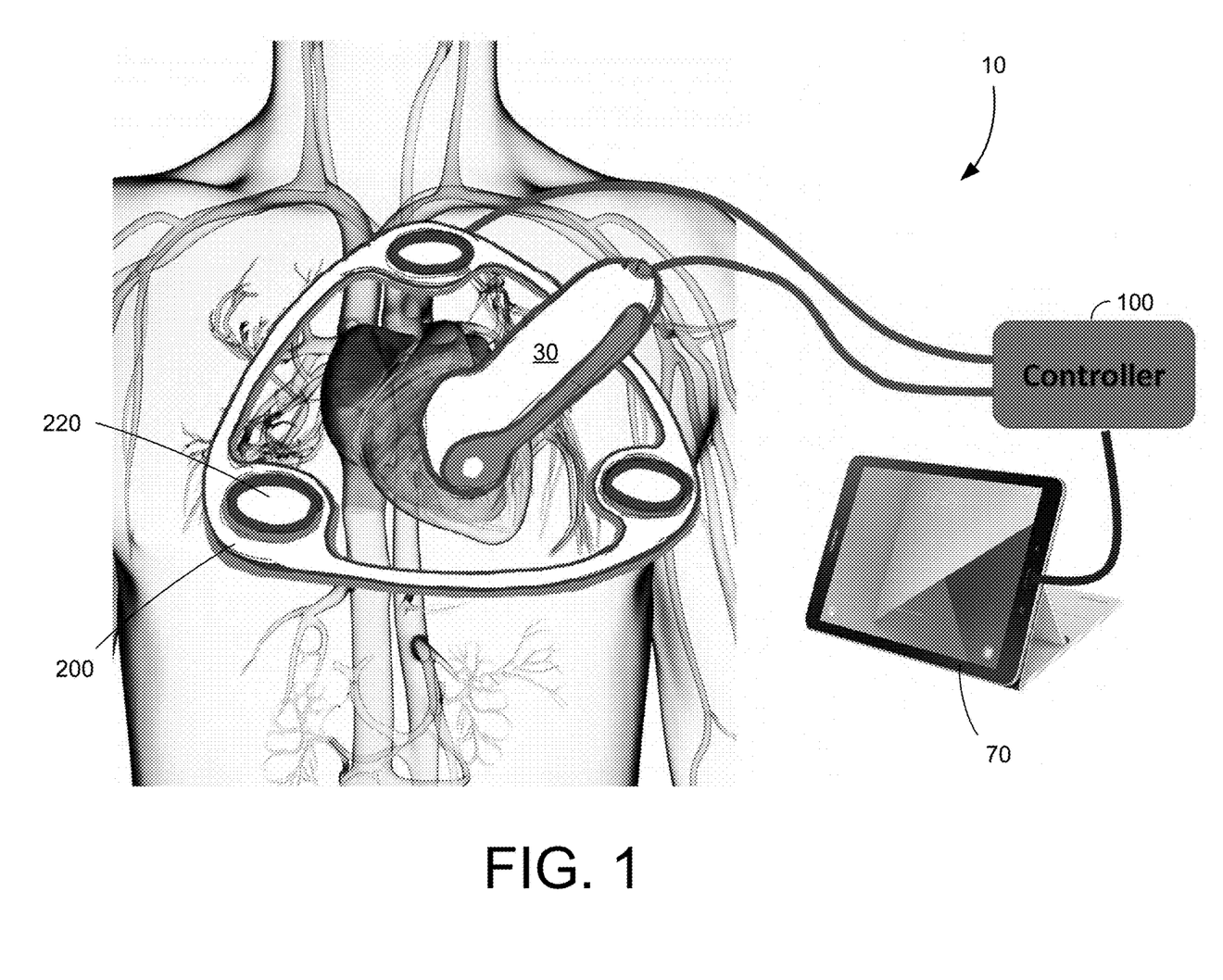
FIG. 1 is a diagram showing an embodiment of a multi-modal heart diagnostic system.

FIG. 1 shows an embodiment of a system to monitor heart activity and assist medical personnel in performing diagnostic procedures of the heart. The system 10 includes a positioning/reference device 200 with several multi-modal sensors (also referred to as sensor units) 220. The positioning device 200 of FIG. 1 shows three multi-modal sensors 220, but fewer multi-modal sensors 220 or additional multi-modal sensors can be used in other embodiments. The positioning device 200 can be in communication with (either by a wired or wireless connection) a controller 100 to permit the controller 100 to receive signals and/or data from the multi-modal sensors 220 of the positioning device 200 and to synchronize the data from the multi-modal sensors 220 as needed. In another embodiment, the individual multi-modal sensors 220 may be individually in communication with the controller 100. The system 10 includes a hand-held probe 30 for performing echocardiography. The probe 30 can be in communication with (either by a wired or wireless connection) the controller 100 to permit the controller 100 to receive signals and/or data from the probe 30. The controller 100 can be in communication with (either by a wired or wireless connection) a display 70 in order for the controller 100 to provide the information obtained from the probe 30 and the multi-modal sensors 220 to the user of the system 100. In addition, the display 70 may include a user interface (e.g., a touch panel) to permit the operator to input information and/or instructions to the controller 100. In an embodiment, the display 70 may be a liquid crystal display (LCD) but may be a desktop, laptop or tablet computer or a hand-held device, such as a cellular telephone (e.g., smartphone), in other embodiments. In another embodiment, the display 70 can be a thin flexible display that can be placed directly on the chest of the person (or patient) to represent anatomical structures of the person located beneath the flexible display.

Figure 2:
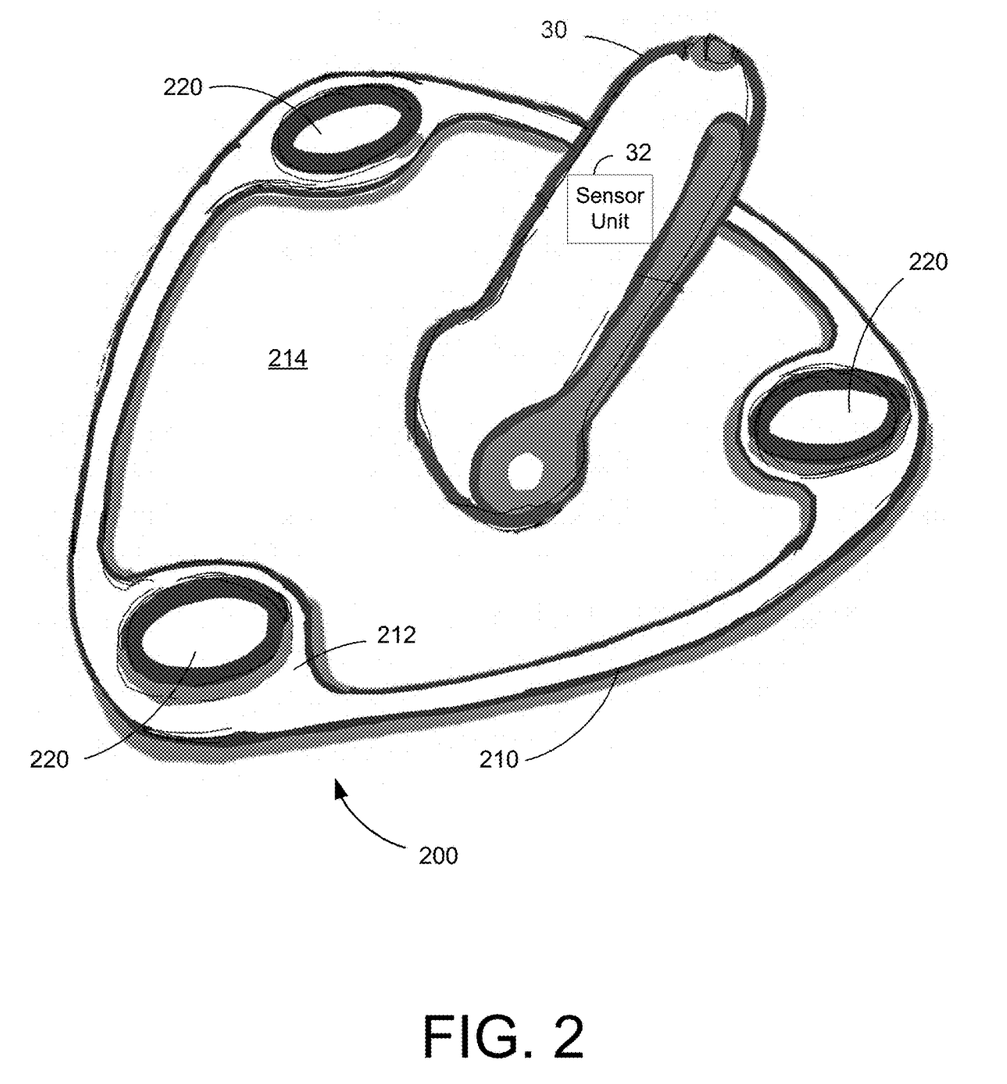
FIG. 2 is a diagram showing an embodiment of the positioning device and probe of FIG. 1.

FIG. 2 shows an embodiment of the positioning system 200 and probe 30. The positioning system 200 can include a support structure 210 having a generally curvilinear triangle (or a Reuleaux triangle) shape. While a curvilinear triangle shape for the support structure 210 is shown in FIG. 2, the support structure 210 can have other geometric shapes (e.g., circular) and non-geometric shapes in other embodiments. In one embodiment, the support structure 210 can be a soft, flexible material, but may be a rigid or semi-rigid material in other embodiments. The support structure 210 can have a hollow or open interior portion 214 (i.e., an open space or cavity) that permits the probe 30 to move within the support structure 210 and along a person's body when the support structure 210 is placed on the person. However, in other embodiments, the interior portion 214 may be formed from the same material as the other portions of the support structure 210 (i.e., the support structure 210 is a solid piece without an open space) or may incorporate a different material (e.g., a film-like material) different from the other portions of the support structure 210 that may facilitate movement of the probe 30 within the support structure 210 and along the person. In addition, the support structure 210 can incorporate expanded portions 212 at each of the "corners" of the curvilinear triangle shape to hold a multi-modal sensor 220. The expanded portions 212 can be located in the support structure 210 to provide a fixed distance between the multi-modal sensors 220 and to maintain the relative position of the multi-modal sensors 220 in the support structure 210.

In an embodiment, the support structure 210 may provide either printed signs or other indicia that can assist the operator in positioning the support structure 210 on the person undergoing the procedure or in positioning the probe 30 relative to the multi-modal sensors 220 on the body of the person. In another embodiment, display 70 or LED indicators on the support structure 210 can be used to guide the operator during positioning of the support structure 210 to obtain optimal performance of the multi-modal sensors 220. In still another embodiment, artificial intelligence or machine learning algorithms can be used to automatically determine optimal positioning of the support structure 210 and multi-modal sensors 220. The display 70 or LED indicators on the support structure 210 can be used to guide the operator during positioning of the support structure 210 as determined by the artificial intelligence or machine learning algorithm. In an embodiment, after being positioned on the person's body, the support structure 210 may be fastened to the person's body using chemical (e.g., a disposable adhesive similar to that used with standard ECG electrodes) or mechanical (e.g., suction cup) techniques to maintain the position of the support structure 210 on the person's body.

Figure 3:
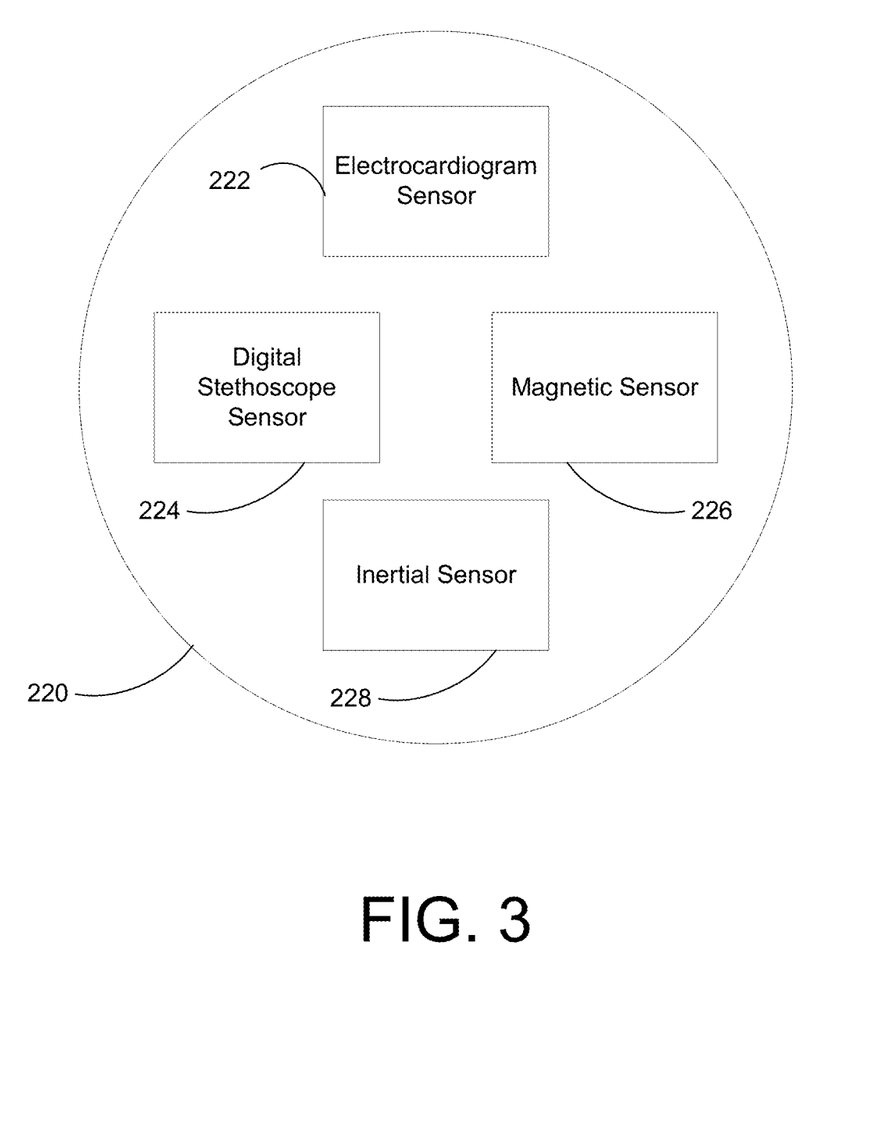
FIG. 3 is a block diagram showing an embodiment of the multi-modal sensor of FIG. 2.

FIG. 3 shows an embodiment of the multi-modal sensor 220. As shown in FIG. 3, the multi-modal sensor 220 can include an electrocardiogram sensor (or electrode) 222 that can be used for capturing an electrocardiogram, a digital stethoscope (DS) sensor 224 that can be used for performing electronic auscultation, a magnetic sensor 226 (e.g., a magnetometer) and an inertial sensor 228 (e.g., an accelerometer). In one embodiment, the inertial sensor 228 can provide dynamic information about the motion and orientation of an object and can be used to measure heart induced motion using ballistocardiography (BCG). While the multi-modal sensor 220 of FIG. 3 is shown with 4 sensors, the multi-modal sensor 220 could include additional sensors, fewer sensors or different sensors in other embodiments. For example, the multi-modal sensor 220 may utilize other motion sensors, such as gyroscopes or proximity sensors, or any other suitable sensor for determining position or orientation either in place of or in addition to inertial sensors 228 and magnetic sensors 226. In other embodiments, other suitable techniques and devices (e.g., RF and/or NFC positioning techniques and devices) for determining position and orientation may be used.

The three multi-modal sensors 220 of the support structure 210 can provide the controller 100 with three (3) channels of ECG readings (e.g., between the ECG electrodes 222 of the first and second multi-modal sensors, between the ECG electrodes 222 of the second and third multi-modal sensors and between the ECG electrodes 222 of the third and first multi-modal sensors). Each ECG electrode 222 provides a contact for the differential bioamplifier used in generating the ECG. In another embodiment using a solid support structure 210, a reference electrode for the ECG can be placed in the center of the support structure 210 that can create 3 additional ECG channels between the reference electrode and the ECG electrodes 222 of the multi-modal sensors 220. The multi-modal sensors 220 can also provide the controller 100 with 3 audio signals (1 from each DS sensor 224), 3 BCG signals (1 from each inertial (or BCG) sensor 228) and 3 3D orientation signals (1 from each magnetic sensor 226). In addition, the controller 100 can receive ultrasound images from the probe 30 and a position and/or orientation of the probe 30 from a sensor unit 32 (see FIG. 2) located in or on the probe 30. The probe 30 can either incorporate the sensor unit 32 within the body of the probe 30 or the sensor unit 32 can be attached to the exterior of a conventional probe. In an embodiment, the sensor unit 32 can include one or more motion sensors such as inertial sensors (e.g., accelerometers), gyroscopes, magnetic sensors (e.g., magnetometers), proximity sensors, any other suitable sensor for determining position or orientation, or any combination thereof. In other embodiments, other suitable techniques and devices (e.g., RF and/or NFC positioning techniques and devices) for determining the position and orientation of the probe 30 may be used.

Figure 4:
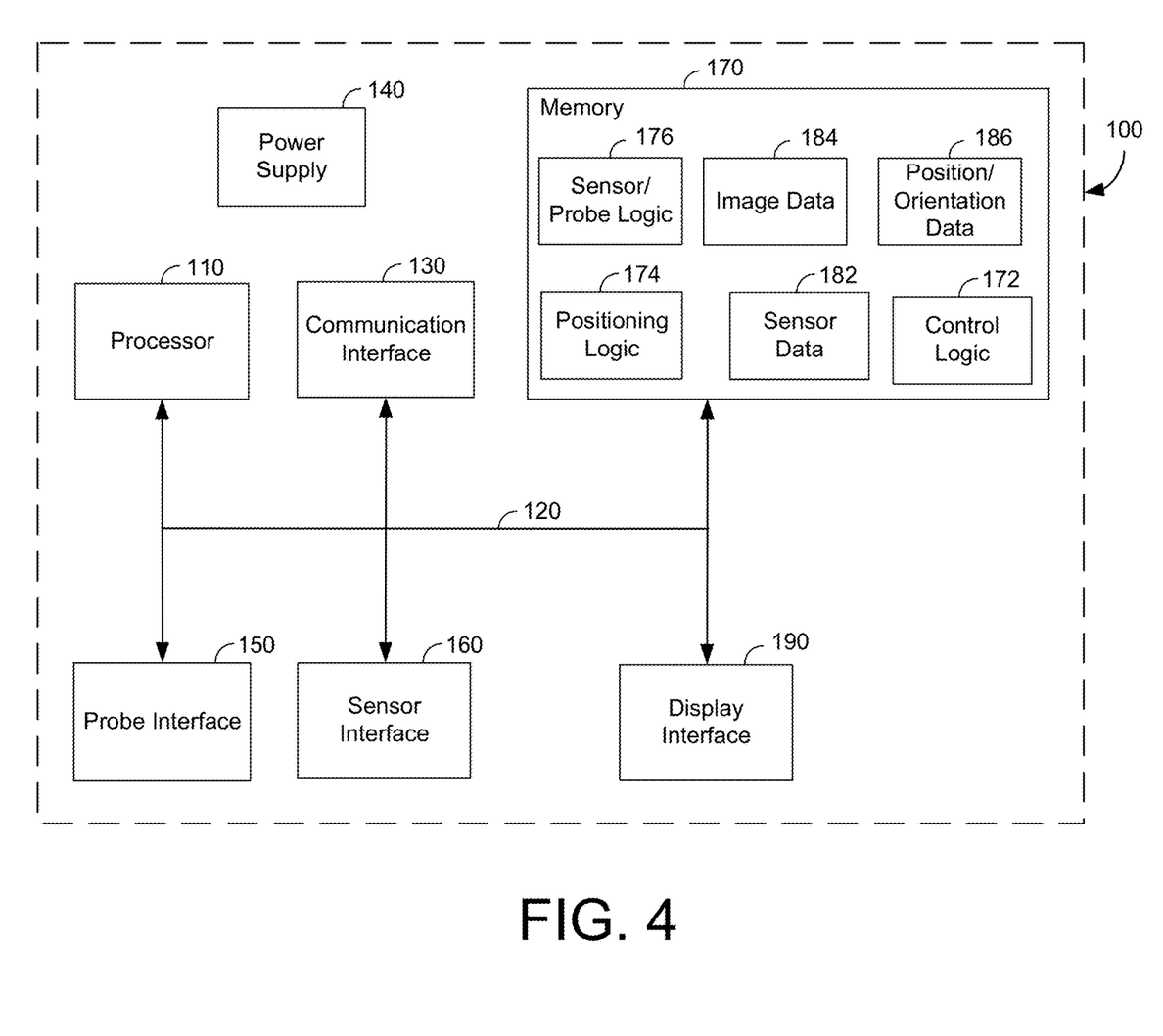
FIG. 4 is a block diagram showing an embodiment of a controller of FIG. 1.

FIG. 4 shows an embodiment of the controller 100. The controller 100 shown by FIG. 4 can include logic 172, referred to herein as "control logic," for generally controlling the operation of the controller 100. The controller 100 also includes logic 174, referred to herein as "positioning logic," and logic 176, referred to herein as "sensor/probe logic." The positioning logic 174 can be used for calibrating operation of the probe 30 in the positioning system 200 and for providing guidance or feedback to the operator of the probe in order to permit the operator to position the probe 30 within the positioning system 200 for an EC. The sensor/probe logic 176 can be used to process signals, images, data, etc. received from the probe 30 and the multi-modal sensors 220. In other embodiments, the positioning logic 174 and/or the sensor/probe logic 176 can be combined with the control logic 172 or with one another. The control logic 172, the positioning logic 174 and the sensor/probe logic 176 may be implemented in software, firmware, hardware, or any combination thereof. In FIG. 4, control logic 172, the positioning logic 174 and the sensor/probe logic 176 are implemented in software and stored in memory 170. However, other configurations of the control logic 172, the positioning logic 174 and the sensor/probe logic 176 are possible in other embodiments.

Note that the control logic 172, the positioning logic 174 and the sensor/probe logic 176, when implemented in software, can be stored and transported on any computer-readable medium for use by or in connection with an instruction execution apparatus that can fetch and execute instructions. In the context of this document, a "computer-readable medium" can be any non-transitory means that can contain or store code for use by or in connection with the instruction execution apparatus.

The controller 100 may include at least one conventional processor 110, which includes processing hardware for executing instructions stored in the memory 170. As an example, the processor 110 may include a central processing unit (CPU) or a digital signal processor (DSP). The processor 110 communicates to and drives the other elements within the controller 100 via a local interface 120, which can include at least one bus. When the control logic 172, the positioning logic 174 and the sensor/probe logic 176 and are implemented in software, the processor 110 may execute instructions of the control logic 172, the positioning logic 174 and the sensor/probe logic 176 to perform the functions ascribed herein to the control logic 172, the positioning logic 174 and the sensor/probe logic 176.

The controller 100 also has a communication interface 130. The communication interface 130 includes a radio frequency (RF) radio or other device for communicating wirelessly and corresponding connection ports for wired communications (e.g., Ethernet). Using the communication interface 130, the controller 100 may communicate with other devices, systems (e.g., the electronic medical record (EMR) software of a medical facility) and/or networks (e.g., the Internet).

The controller 100 can have a power supply 140, which provides electrical power to the components of the controller 100 and possibly to the probe 30 and/or the multi-modal sensors 220 of the positioning system 200 in an embodiment. In one embodiment, the power supply 140 has an interface that allows it to plug into or otherwise interface with an external component, such as a wall outlet or battery, and receive electrical power from such external component. If desired, the power supply 140 may incorporate one or more batteries to permit the controller 100 to be independent of the external power component.

The controller 100 can include a probe interface 150, a sensor interface 160 and a display interface 190. In one embodiment, the probe interface 150 and the sensor interface 160 may be combined into a single interface. The probe interface 150 enables the controller 100 to exchange (e.g., send and receive) signals and data with the probe 30. For example, the probe 30 can provide image data to the controller 100 during a procedure that is then stored in image data 184. In addition, the inertial sensor and the magnetic sensor of the probe 30 can provide position and orientation information that is stored in position/orientation data 186. The sensor interface 160 enables the controller 100 to exchange (e.g., send and receive) signals and data with the multi-modal sensors 220 of the positioning device 200. For example, the multi-modal sensors 220 can provide data from individual sensors to the controller 100 that is then stored in sensor data 182. The display interface 190 enables the controller 100 to exchange (e.g., send and receive) data and information with the display 70. For example, the controller 100 may provide image data 184 from the probe 30 to the display 70 via the display interface 190 for viewing by the operator. Each of the probe interface 150, sensor interface 160 and the display interface 190 may include any suitable interfaces for providing signals and data between processor 110 and the corresponding component connected to the interface. The interfaces may include communication busses such as I2C, SPI, USB, UART, and GPIO. In some embodiments, the sensor interface 160 may also include connections such that signals from the multi-modal sensors 220 (e.g., measured analog signals) may be provided to processor 110.

The sensor/probe logic 176 of the controller 100 can extract different types of information from the set of signals and/or data received from the multi-modal sensors 220 and stored as sensor data 182. The sensor/probe logic 176 can determine a common component of all sensors of the same type (e.g., ECG sensors 222, DS sensors 224, or inertial (or BCG) sensors 228). The sensor/probe logic 176 can also determine the latency of individual signals of the same kind (e.g., between different ECG sensors 222) or between different signals of the same multi-modal sensor 220 (e.g., between an ECG sensor 222 and an inertial (or BCG) sensor 228) or, more specifically, as a time delay between different signals of different multi-modal sensors 220 (e.g., between a first ECG sensor 222 and a second inertial (or BCG) sensor 228).

Further, the sensor/probe logic 176 can determine the total power of individual signals or event related energy of the signals. For the DS sensors 224, the sensor/probe logic 176 can determine the PDSx—the power of an individual DS sensor 224, or the power during the heart beat events, for example, sounds S1 (PDS1 for a first DS sensor 224) and S2 (PDS2 for a second DS sensor 224). For the ECG sensors 222, the sensor/probe logic 176 can determine the total power or event related power (e.g., ECGP—the power of the P-wave, or other events of interest, such as Q, R, S and T waves). In addition, the sensor/probe logic 176 can calculate a related power estimate for each event as the maximum amplitude during the event, or as an average value during the event (e.g., an RMS value of the signal). In an embodiment, each event related energy can be calculated as integral of the signal (or signal squared) over event time. The sensor/probe logic 176 can also be used to detect turbulent flow (i.e., recirculation of fluids) in the heart that may be a result of stenosis (and possibly determine a location of the stenosis) using the signals from the DS sensors 224 and the ECG sensors 222. In an embodiment, the sensor/probe logic 176 can perform a pre-ejection analysis (e.g., ECG to BCG/accelerometer 4 electrical signal to mechanical motion latency) having a better signal to noise ratio (common component ICA of signals of the same type from different sensors)).

The use of the positioning device 200 for different diagnostic conditions may result in the positioning device 200 having different optimal positions. In one embodiment, the optimal position for the positioning device 200 can be determined by the sensor/probe logic 176 using the relative weights of individual signals for the multi-modal sensors 220. For example, some condition may require positioning of the positioning device 200 that results in the signal with 60% contribution from the first ECG sensor 222, 25% contribution from the second ECG sensor 222, and 15% contribution from the third ECG sensor 222. The controller 100 may guide the operator to move the positioning device 200 until the maximum value of the desired composite signals is achieved. Guidance of the operator can be performed through the display 70 or indicators on the positioning device 200 itself indicating the desired direction of the motion and the desired rotational position for the positioning device 200 needed to place the positioning device 200 in the optimum position.

Figure 5:
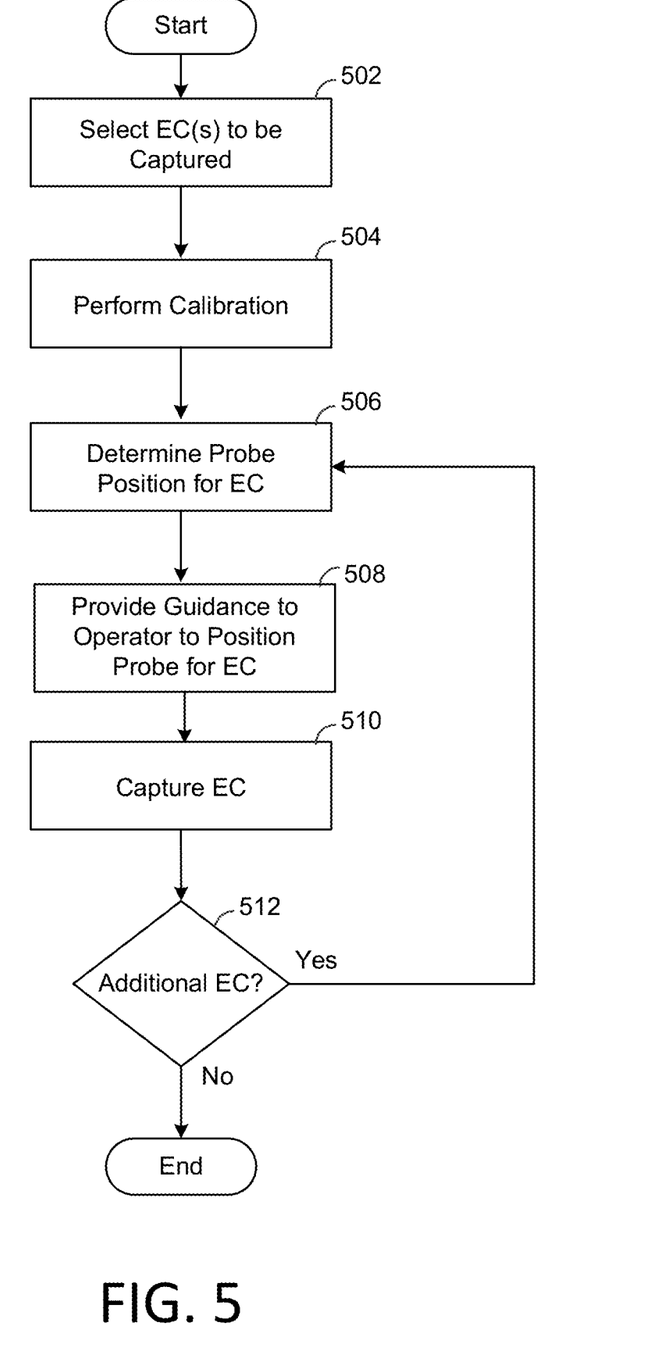
FIG. 5 is a flow diagram of an embodiment of a process for capturing an echocardiogram with the probe.

The positioning logic 174 can be used to provide guidance to an operator of the system 10 in placing the probe 30 on the person's body in an appropriate (or optimal) position to capture a desired EC once the positioning device 200 is in the desired position. FIG. 5 shows an embodiment of a process executed by the positioning logic 174 to determine an appropriate position for the probe 30 in the positioning device 200 to capture a desired EC. The process begins by the operator of the system 10 selecting one or more ECs to capture (step 502). In one embodiment, the ECs that may be captured can include a parasternal view (long axis and/or short axis), a subxiphoid view and/or an apical view.

Figure 6:
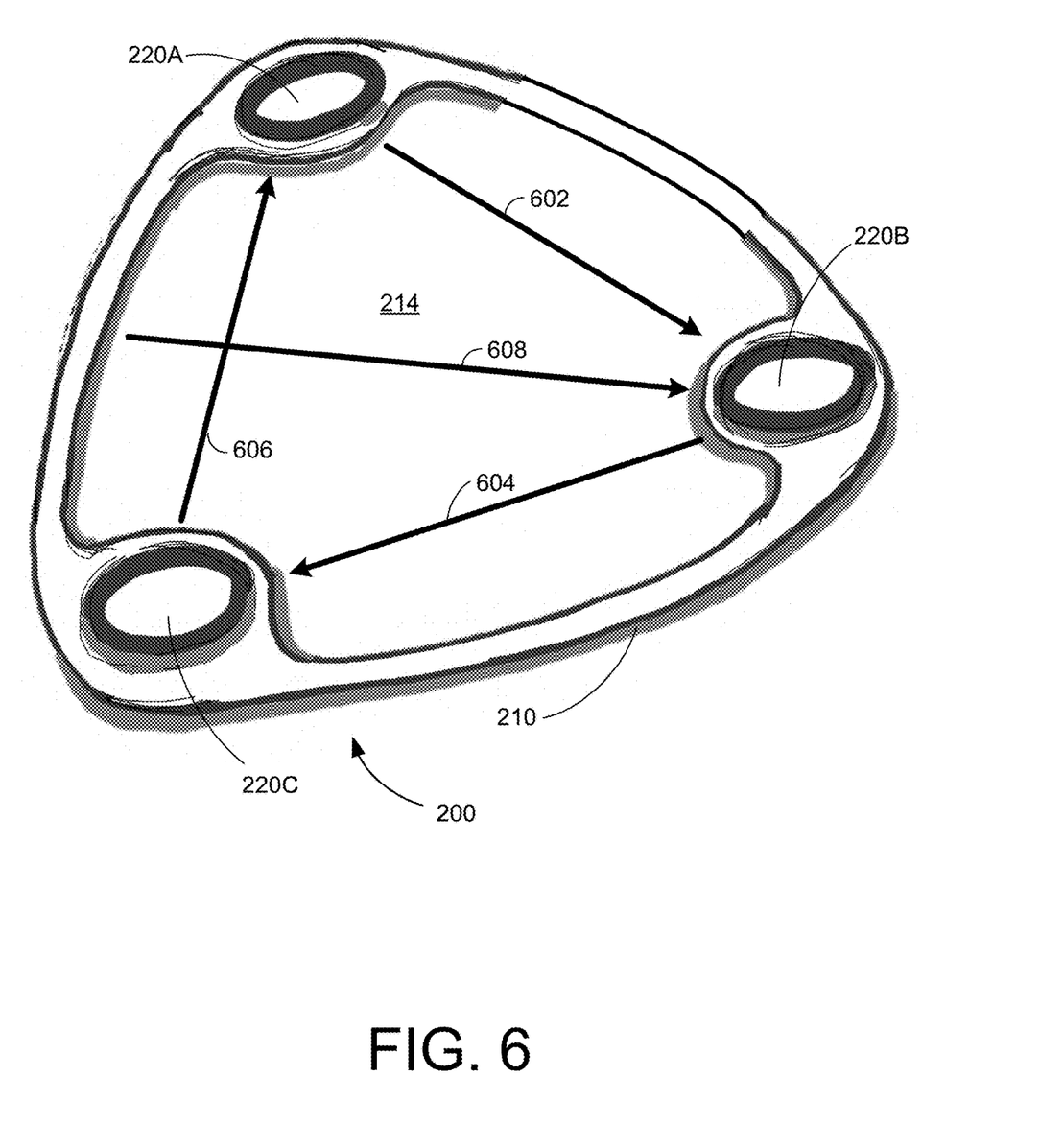
FIG. 6 is a diagram showing an embodiment of probe sweeps within the positioning device to calibrate the diagnostic system.

Once the operator has selected the ECs to be captured, the operator has to calibrate the system 10 (step 504). The calibration of the system 10 involves the movement of the probe 30 within the positioning device 200 to obtain information for the positioning logic 174 to determine the appropriate position for the probe 30 in the positioning device 200 for the selected ECs to be captured. The operator can perform several sweeps of the probe 30 within the positioning device 200 during calibration. FIG. 6 shows a first path 602 for the sweep of the probe 30 within the positioning device 200 that extends between multi-modal sensor 220A and multi-modal sensor 220B, a second path 604 for the sweep of the probe 30 within the positioning device 200 that extends between multi-modal sensor 220B and multi-modal sensor 220C, a third path 606 for the sweep of the probe 30 within the positioning device 200 that extends between multi-modal sensor 220C and multi-modal sensor 220A, and a fourth path 608 for the sweep of the probe 30 within the positioning device 200 that extends from a point midway between multi-modal sensor 220A and multi-modal sensor 220C to multi-modal sensor 220B and typically corresponds to the preliminary movement of the probe 30 by an expert in a typical EC procedure.

Figure 7:
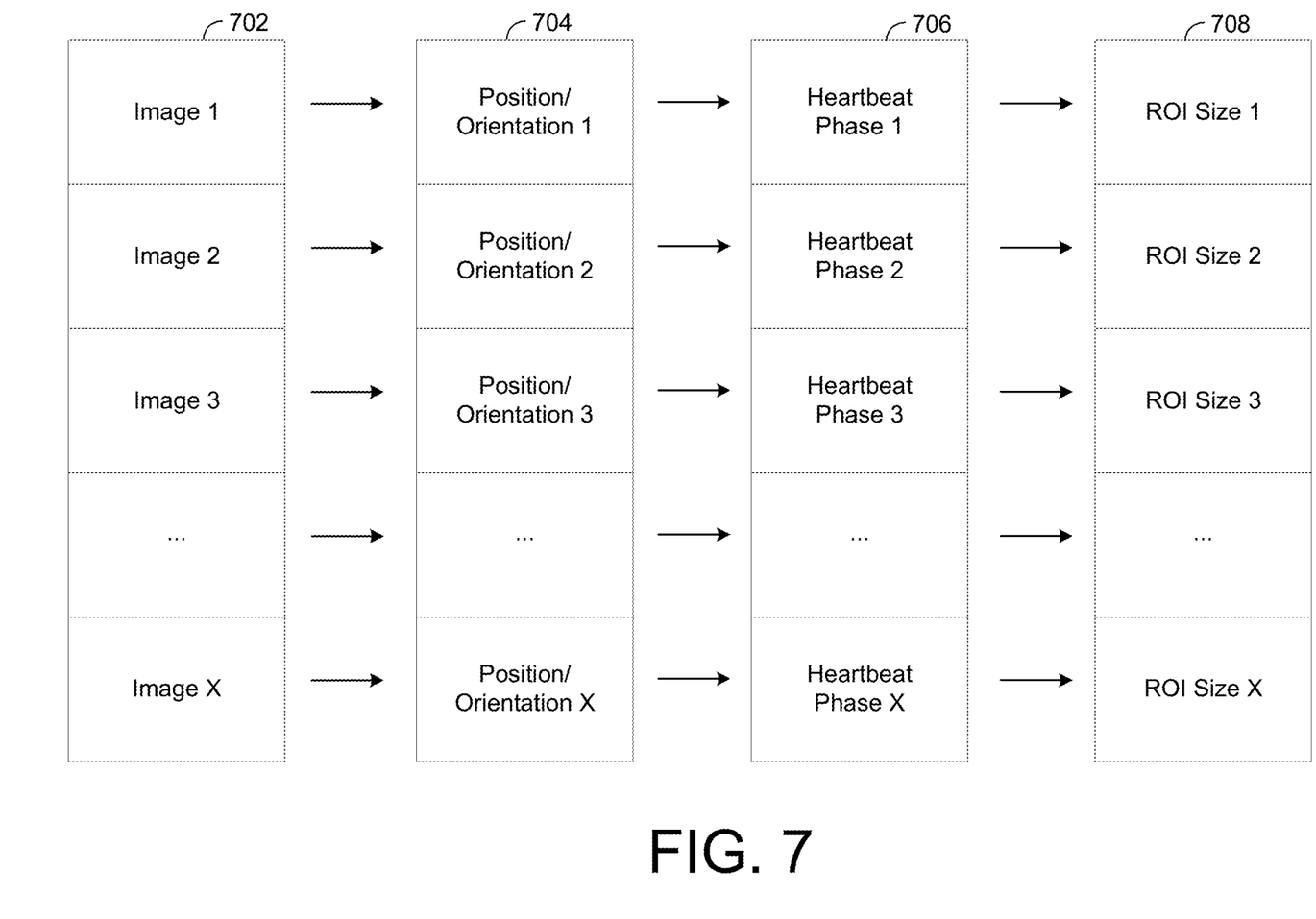
FIG. 7 is a diagram showing the relationship between images and position/orientation information obtained during a probe sweep.

During each sweep of the probe 30 in the positioning device 200, a series of images can be captured from the probe 30 along with corresponding location information regarding the probe 30, and a relative phase of the heartbeat as determined using ECG, BCG and sound information captured by multi-modal sensors 220. The sweep of the probe 30 can capture several heartbeats in order to determine when the ventricles are open (as opposed to contracted), which facilitates a better view of the ventricles. The same method can be applied for the atrium, which corresponds to the different phase of the heartbeat. As shown in FIG. 7, each captured image from the sweep of the probe can be stored in an image set 702 and corresponding location information of the probe for each captured image can be stored in a position/orientation data set 704, and the relative phase of the heartbeat, which is generated from the sensor data 182, can be stored in heartbeat phase data set 706. The image set 702 from each sweep of the probe 30 can be stored in image data 184 and the position/orientation data set 704 from each sweep of the probe 30 can be stored in position/orientation data 186. The position/orientation data set 704 can include, for each captured image in image set 702, an x-y position of the center of the probe 30 relative to the positioning device 200 (e.g., as determined by triangulation using 3D orientation signals in one embodiment), a rotational orientation of the probe 30 about the center and an angular orientation of the probe 30 relative to the plane of the positioning device 200. A size of the region of interest (e.g., an area of cross section of the heart) can be calculated and stored in the region of interest (ROI) size data set 708. In an embodiment, the relative angle of the probe 30 can be determined from the absolute 3D angle of the probe 30 (as determined by a 3D orientation signal from the magnetic sensor in the probe 30) and from 3D orientation signals from the individual sensors (e.g., magnetic sensors 226) in the multi-modal sensors 220. The position/orientation data associated with each captured image can be obtained from the inertial sensor and magnetic sensor of the probe 30 and/or the multi-modal sensors 220 (including inertial sensors 228 and magnetic sensors 226). However, in another embodiment, the position/orientation data associated with each captured image can be obtained only from the inertial sensor and the magnetic sensor of the probe 30. The position/orientation data can be defined relative to reference points of the support structure 210 corresponding, in one embodiment, to the location of the multi-modal sensors 220.

After the image set 702, the position/orientation data set 704, the heartbeat phase data set 706, and the ROI size data set 708 is captured for each sweep of the probe 30 during calibration, the positioning logic 174 can determine an appropriate location for the probe 30 within the positioning device 200 and relative to the multi-modal sensors 220 (or reference points) for a selected EC to be captured (step 506). The positioning logic 174 can then use the image sets 702, the position/orientation data sets 704, heartbeat phase data set 706, and the ROI size data set 708 from each of the sweeps of the calibration process to determine an optimal position and orientation of the probe 30 for capturing the desired view of the EC (e.g., the cross section of the ventricles). The positioning logic 174 can use information from the image sets 702 and the relative phase of the heartbeat from heartbeat phase data set 706 to determine the location of the heart in the person's chest and then use the approximate location of the heart to determine the position of the probe 30 relative to the location of the heart needed to capture the desired view of the echocardiogram. In an embodiment, the positioning logic 174 can use the image sets 702, the relative phase of the heartbeat from heartbeat phase data set 706 and the ROI size data set 708 to create a three-dimensional (3D) model of the heart in the person's chest with respect to the reference points of the positioning device 200. The positioning logic 174 can then use the 3D model of the heart in determining where to locate the probe 30 for the desired EC. In one embodiment, the positioning logic 174 can use a machine learning or artificial intelligence algorithm with the image sets 702 and the position/orientation data sets 704 from the calibration process to determine the appropriate position. The positioning logic 174 can include a training set that includes prior image sets 702 and position/orientation data sets 704 along with the position chosen for the desired EC to train the machine learning or artificial intelligence algorithm.

As known in the art, "machine learning" generally refers to neural computing techniques or artificial intelligence whereby a computer effectively "learns" relationships between inputs and outputs. In one embodiment, the positioning logic 174 employs an appropriate algorithm (e.g., random forest, support vector machines, Bayes, logistic regression, etc.) in order to determine an optimal position and orientation for the probe 30 that results in an optimal EC. In learning the optimal position and orientation of the probe 30, the positioning logic 174 performs an analysis on the image data 184, the position/orientation data 186, and the relative phase of the heartbeat generated from sensor data 182 in order to define relationships between the position and orientation of the probe 30 as indicated by the position/orientation data 186 and the desired output (e.g., a captured EC) as indicated by the image data 184. Then, as the image sets 702, the position/orientation data sets 704 and the heartbeat phase data sets 706 are received during the calibration process, the positioning logic 174 can use the defined relationships to determine the optimal position and orientation of the probe 30 to obtain the desired EC.

In another embodiment, the positioning logic 174 can use information from the multi-modal sensors 220 (e.g., information from the electrocardiogram sensors 222, the digital stethoscope sensors 224 and the inertial sensors 228) to determine an approximate location of the person's heart in the person's chest. The positioning logic 174 can then use the information regarding the approximate location of the heart from the multi-modal sensors 220 along with the image sets 702, the position/orientation data sets 704, heartbeat phase data set 706, and ROI size data set 708 to determine a location for the probe 30 that coincides with the expected location of the features of the heart that are of interest to the operator.

Figure 8:
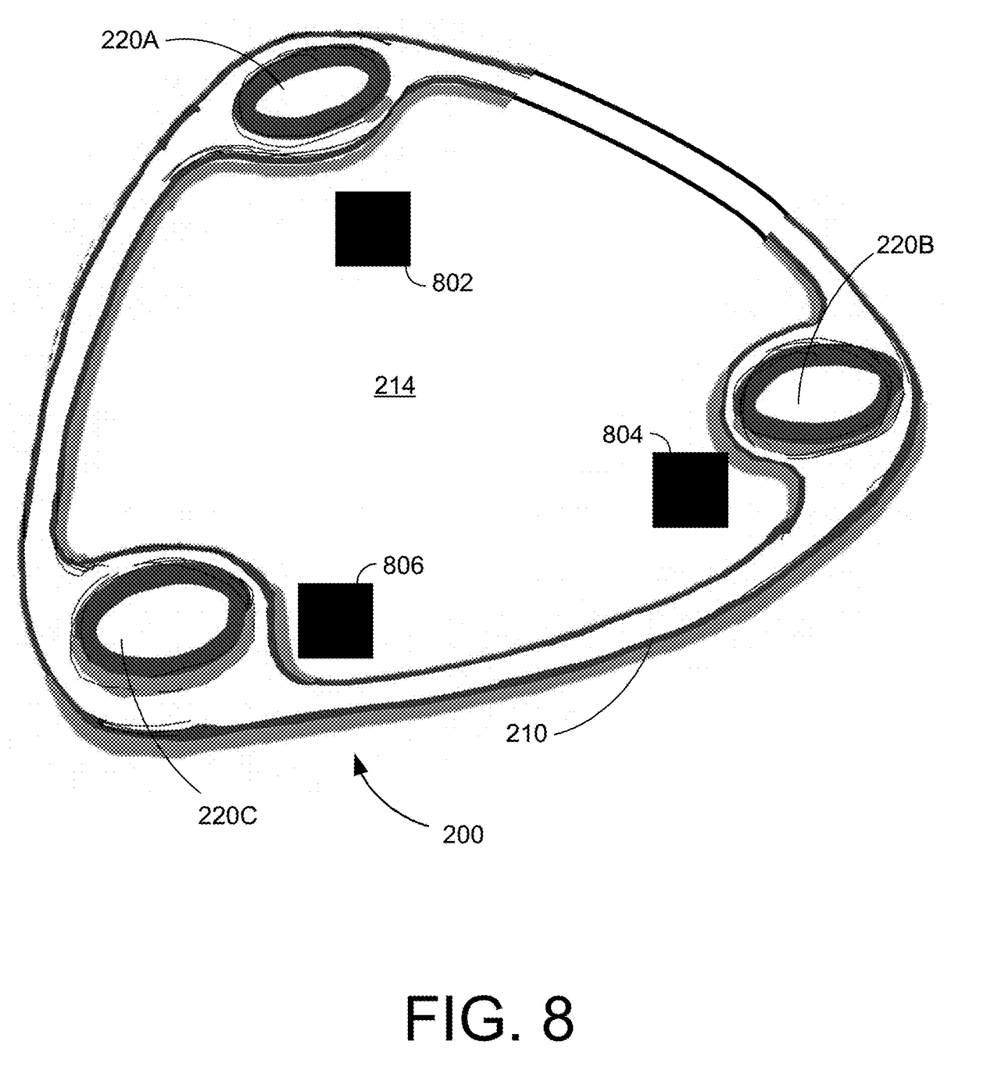
FIG. 8 is a diagram showing an embodiment of appropriate positions for the probe for capturing different echocardiograms.

Once the appropriate position for the probe has been determined, the system 10 can provide guidance to the operator in locating the probe 30 in the positioning device 200 for the desired EC (step 508) using the multi-modal sensors 220 (and their corresponding signals) to provide points of reference. FIG. 8 shows the appropriate positions for the probe 30 in the positioning device 200 for several different ECs. The probe 30 can be positioned at location 802 for a parasternal view, at position 806 for a subxiphoid view, and at position 804 for an apical view. In one embodiment, the positioning logic 174 can provide information to the display 70 (e.g., a computer generated representation of the probe 30 relative to the positioning device 200) to assist the operator in moving the probe 30 into the appropriate position for the desired EC. In another embodiment, LED indicators on the support structure 210 can be used to guide the operator during positioning of the probe 30.

Figure 9:
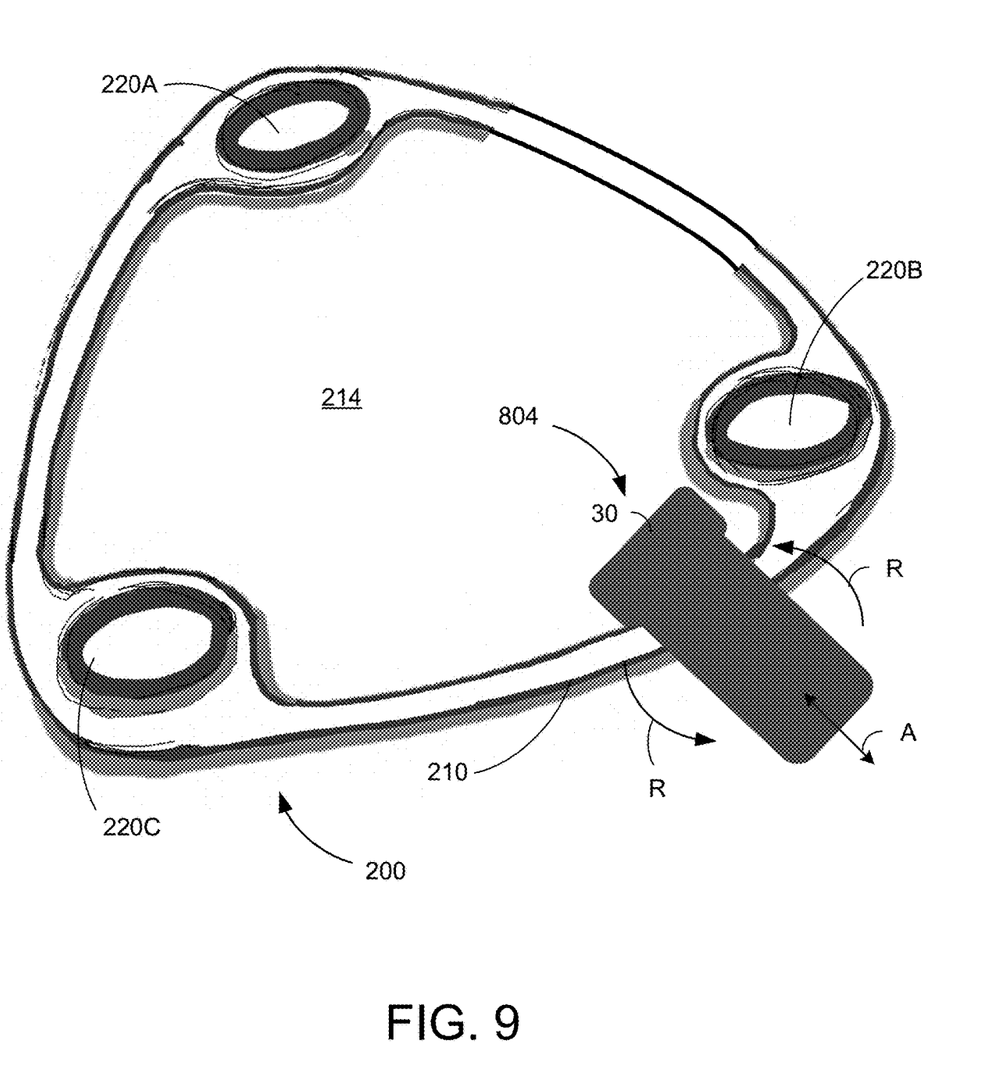
FIG. 9 is a diagram showing an embodiment of the positioning of the probe for capturing an echocardiogram.

After the probe 30 is in the appropriate position, the positioning logic 174 can provide further information to the display 70 (or on the support structure 210) to assist the operator in obtaining the appropriate rotational and angular orientation of the probe 30. For example, as shown in FIG. 9, once the probe 30 is positioned in position 804, the positioning logic 174 can provide additional guidance to the operator on the display 70 to appropriately orient the probe 30 to obtain the desired EC. The positioning logic 174 may have the operator adjust the rotational position of the probe 30 as shown by arrows R (i.e., turn the probe 30 either clockwise or counterclockwise about the center of the probe 30) and/or adjust the angular position of the probe 30 as shown by arrow A (i.e., tilt the probe 30 either toward the operator or away from the operator). In another embodiment, once the probe 30 is at the position and orientation determined by the positioning logic 174, the positioning logic 174 can perform an image analysis of an image captured by the probe 30 at that position and then provide the operator with instructions to make incremental position and/or orientation changes to the probe 30 to improve the quality of the captured image from the probe 30. The incremental changes to the position and/or orientation of the probe 30 can be repeated until an optimal image is obtained from the probe 30. Optimization might include processing of images to calculate the size of the region of interest for the given phase of the heartbeat. Automatic image processing can generate better accuracy in calculating features of interest than the user would be able to perceive.

After the probe 30 is at the proper position and orientation in the positioning device 200, the operator can capture the desired EC (step 510). Next, a determination is made if additional ECs need to be captured (step 512). If no additional ECs are needed, the process ends. However, if additional ECs are required, the process returns to step 506 to determine the probe position for the next EC and the process continues as discussed above until all of the desired ECs have been captured.

Figure 10A:
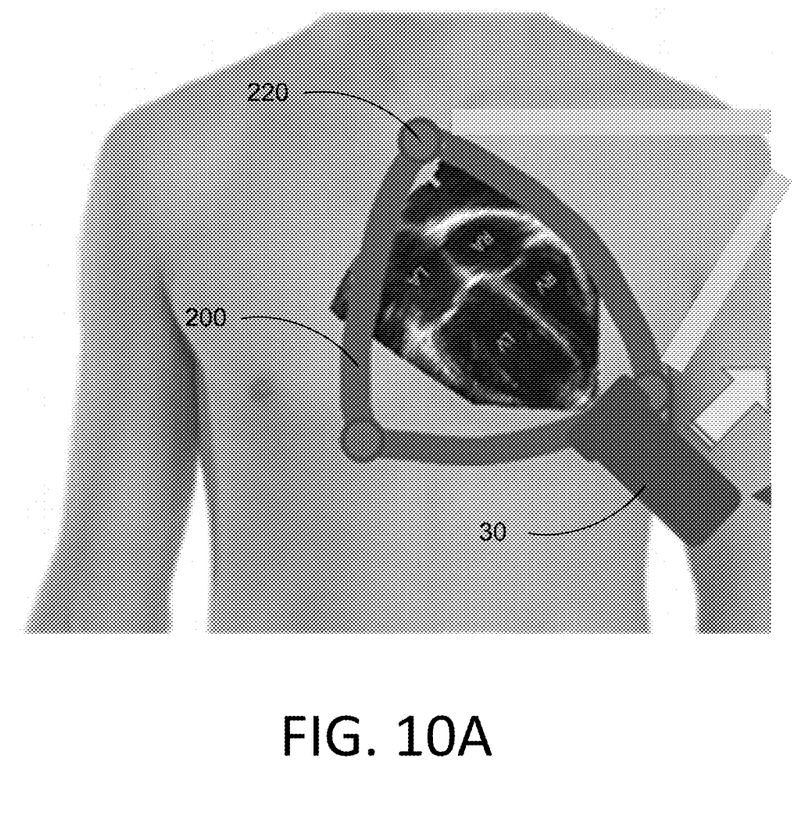
FIG. 10A is a diagram showing an embodiment of an orientation of an echocardiogram image that may be presented to an operator.
Figure 10B:
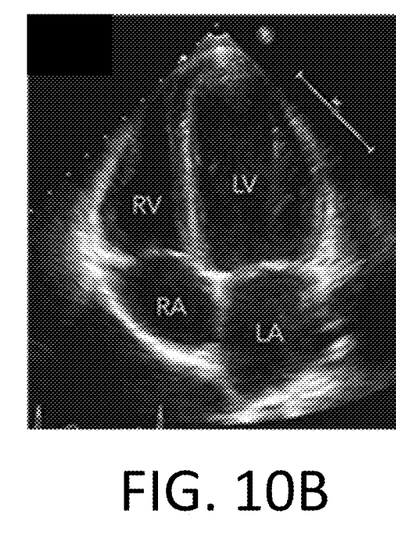
FIG. 10B is a diagram showing a traditional orientation of an echocardiogram image that may be presented to an operator.

The controller can present the captured EC image from the probe 30 to the operator on the display 70. The view of the EC image can be presented relative to the probe 30 being located at the top of the image, as shown in FIG. 10B. The operator then has to mentally rotate the EC image to place it on the physical body of the patient and modify position of the probe 30 in order to achieve the best diagnostic quality of the EC image. In an embodiment, the controller 100 can update the 3D orientation of each multi-modal sensor 220 and relative orientation of the probe 30 such that the EC image from the probe 30 is rendered relative to the probe 30 and multi-modal sensors 220 as shown in FIG. 10A. The controller 100 can provide the operator with the option to select (and switch) between the traditional view of the EC image (as shown in FIG. 10B), the alternate view of the EC image (as shown in FIG. 10A), or both views for presentation on the display 70.

In an embodiment, the selected EC image or view can be made static to permit rendering of the probe position only relative to the reference point and patient's body. In that mode, the controller 100 can simulate an "X-ray view" of organs beneath the current position of the probe 30 to permit the operator to more easily find anatomical structures of interest for specific diagnostic procedures. Moreover, the controller 100 can guide the operator to modify the position of the probe 30, while providing the results of the processing and selection of diagnostically optimal images and videos. For example, small changes in the position of the probe 30 might provide better image of the ventricles and automatic calculation of the size of ventricles may provide guidance for the optimal position based on small changes of the area in the EC image that might not be observable by looking at the EC image. Suggested motion for the probe 30 can be visualized as shown in FIG. 10A as an arrow in the direction of the suggested motion. The feedback provided by the controller can be particularly important for non-expert operators, and permit acquisition of expert quality EC images and videos from non-expert operators. The reference points (i.e., the multimodal sensors 220) don't need extremely accurate positioning on the patient's body as the organs can be visualized relative to the reference points, and operator guidance is suggested in relation to the same reference points.

In an embodiment, the multi-modal sensors 220 have magnetic sensors 226 (e.g., a magnetometer) and inertial sensors 228 (e.g., an accelerometer) that permit the sensor/probe logic 176 to determine an absolute orientation of each multi-modal sensor 220. Since, the probe 30 also has a magnetometer and accelerometer as described above, an absolute orientation of the probe 30, as well as an orientation of the probe 30 relative to each multi-modal sensor can be determined by the positioning logic 174. The multi-modal sensors 220 can be placed at defined physical locations on the body of the patient, as shown in FIG. 1, thus the relative orientation of the probe 30 in relation to the physical location of multi-modal sensors 220 can be visualized and rendered for the operator on the display 70 to facilitate guidance of the probe 30 to the optimal recording position and orientation.

In another embodiment, the probe 30 can be equipped with a small magnet with strength significantly larger than Earth's magnetic field. In that case, the 3D vector of magnetic field of each multi-modal sensor 220 would point toward the magnet on the probe 30. By using triangulation of vectors from at least three multi-modal sensors 220, the absolute position of the probe 30 relative to the multi-modal sensors 220, which are used as reference points, can be determined.

In a further embodiment, a reference magnet can be implemented as dynamic electromagnetic coil in the probe that can be turned on to produce an electro-magnetic field only when determining the relative position of the probe 30.

By using this approach, the controller 100 can have the individual multi-modal sensors 220 measure both a 3D vector of Earth's magnetic field (for accurate orientation of the sensors) and the 3D vector of the reference field on the probe 30 (for accurate positioning of the probe 30), and provide the information to the controller 100 for subsequent use by the controller 100.

Although the figures herein may show a specific order of method steps, the order of the steps may differ from what is depicted. Also, two or more steps may be performed concurrently or with partial concurrence. Variations in step performance can depend on the software and hardware systems chosen and on designer choice. All such variations are within the scope of the application. Software implementations could be accomplished with standard programming techniques, with rule based logic and other logic to accomplish the various connection steps, processing steps, comparison steps and decision steps.

It should be understood that the identified embodiments are offered by way of example only. Other substitutions, modifications, changes and omissions may be made in the design, operating conditions and arrangement of the embodiments without departing from the scope of the present application. Accordingly, the present application is not limited to a particular embodiment, but extends to various modifications that nevertheless fall within the scope of the application. It should also be understood that the phraseology and terminology employed herein is for the purpose of description only and should not be regarded as limiting.

What is claimed is:

1. A system for positioning a probe to capture an echocardiogram of a patient, the system comprising:
a positioning device to be placed on a patient, the positioning device comprising a support structure defining an open interior space and a plurality of reference points around the open interior space, wherein the support structure comprises a plurality of sensor units, each sensor unit of the plurality of sensor units being located at a corresponding reference point of the plurality of reference points, each sensor unit of the plurality of sensor units comprises an inertial sensor, a magnetic sensor, and at least one of an electrocardiogram sensor or a digital stethoscope sensor;
a probe configured to capture an echocardiogram image, the probe configured to be moved within the open interior space of the support structure, the probe comprising at least one motion sensor; and
a controller connected to the probe, the controller configured to determine a position for the probe in the open interior space of the support structure with respect to the plurality of reference points and signals from the at least one motion sensor of the probe to capture the echocardiogram image and to provide guidance on a display to an operator to move the probe to the determined position.

2. The system of claim 1, wherein the controller is connected to the plurality of sensor units to receive signals from the inertial sensors and magnetic sensors of the plurality of sensor units and the controller is configured to determine a position for the probe in the open interior space of the support structure using the received signals from the inertial sensors and magnetic sensors of the plurality of sensor units.

3. The system of claim 1, wherein the wherein:
the controller is connected to the plurality of sensor units to receive signals from the inertial sensors, the magnetic sensors, and the at least one of the electrocardiogram sensor or the digital stethoscope sensor of the plurality of sensor units; and the controller is configured to generate one or more of an electrocardiogram, an electronic auscultation or a ballistocardiogram using the received signals from the inertial sensors, the magnetic sensors, and the at least one of the electrocardiogram sensor or the digital stethoscope sensor of the plurality of sensor units.

4. The system of claim 1, wherein the controller is further configured to present the echocardiogram image on the display relative to a location of the probe and a location of the plurality of reference points.

5. The system of claim 1, wherein the controller is configured to determine one or more of a rotational orientation or an angular orientation for the probe at the determined position for the probe.

6. The system of claim 1, wherein the controller is configured to receive a plurality of images from the probe and a plurality of data sets prior to the determination of the position of the probe, wherein each data set of the plurality of data sets corresponds to a position and orientation of the probe within the support structure when an image of the plurality of images is captured, the controller configured to use the plurality of images and the plurality of data sets to determine the position of the probe in the support structure.

7. The system of claim 6, wherein the controller uses a machine learning algorithm having the plurality of images and the plurality of data sets as inputs to determine the position of the probe in the support structure based on relationships between the images, data sets and probe position determined from prior images, data sets and selected probe positions.

8. The system of claim 6, wherein the probe is moved between the plurality of reference points to generate the plurality of images and the plurality of data sets for the controller.

9. The system of claim 6, wherein the controller creates a 3D model of the heart relative to the plurality of reference points in the support structure with the plurality of images and the plurality of data sets.

10. The system of claim 1, wherein the support structure has a substantially curvilinear triangle shape, and the plurality of reference points correspond to points of the curvilinear triangle shape.

11. A method for positioning a probe to capture an echocardiogram of a patient, the method comprising:

placing a positioning device on a patient, the positioning device comprising a support structure defining an open interior space and a plurality of reference points around the open interior space, the support structure comprising a plurality of sensor units, each sensor unit of the plurality of sensor units being located at a corresponding reference point of the plurality of reference points, each sensor unit of the plurality of sensor units comprising an inertial sensor, a magnetic sensor, and an electrocardiogram sensor or a digital stethoscope sensor;

capturing a plurality of images from a probe and a plurality of data sets associated with the probe, wherein each data set of the plurality of data sets corresponds to a position and orientation of the probe within the support structure when an image of the plurality of images is captured, the probe comprising an inertial sensor and a magnetic sensor, and capturing the plurality of data sets associated with the probe includes determining the position and orientation of the probe based on signals from the inertial sensor and magnetic sensor of the probe and signals from the inertial sensors and magnetic sensors of the plurality of sensor units;

determining, by a controller, a position for the probe in the open interior space of the support structure to capture an echocardiogram image based on the plurality of images and the plurality of data sets, wherein the position for the probe is determined with respect to the plurality of reference points;

guiding an operator to move the probe within the open interior space of the support structure to the determined position, wherein guiding an operator to move the probe within the open interior space includes providing information to an operator on a display; and positioning the probe at the determined position to capture the echocardiogram image.

12. The method of claim 11, wherein the capturing a plurality of images and a plurality of data sets with a probe includes moving the probe between the plurality of reference points.

13. The method of claim 11, further comprising presenting the echocardiogram image from the probe on the display, wherein the echocardiogram image is presented relative to a location of the probe and a location of the plurality of reference points.

14. The method of claim 11, wherein positioning the probe at the determined position includes setting one or more of a rotational orientation or an angular orientation for the probe at the determined position for the probe.

15. The method of claim 11, further comprising generating one or more of an electrocardiogram, a ballistocardiogram or an electronic auscultation using signals from the inertial sensors, the magnetic sensors, the electrocardiogram sensors and the digital stethoscope sensors of the plurality of sensor units.

16. The method of claim 11, further comprising:

creating a 3D model of the heart relative to the plurality of reference points in the support structure with the plurality of images and the plurality of data sets; and wherein determining, by the controller, a position for the probe in the open interior space of the support structure includes determining the position for the probe using the 3D model of the heart.

\* \* \* \* \*